(12) United States Patent
Matiskella et al.

(10) Patent No.: US 7,829,711 B2
(45) Date of Patent: Nov. 9, 2010

(54) CRYSTALLINE MATERIALS OF 1-(4-BENZOYL-PIPERAZIN-1-YL)-2-[4-METHOXY-7-(3-METHYL-[1,2,4]TRIAZOL-1-YL)-1H-PYRROLO[2,3-C]PYRIDINE-3-YL]-ETHANE-1,2-DIONE

(75) Inventors: John D. Matiskella, Wallingford, CT (US); Chenkou Wei, Princeton Junction, NJ (US); Qi Gao, Franklin Park, NJ (US); Chong-Hui Gu, North Brunswick, NJ (US); Shan-Ming Kuang, Florence, SC (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 12/468,105

(22) Filed: May 19, 2009

(65) Prior Publication Data

US 2009/0227794 A1 Sep. 10, 2009

Related U.S. Application Data

(63) Continuation of application No. 11/267,440, filed on Nov. 4, 2005, now abandoned.

(60) Provisional application No. 60/626,148, filed on Nov. 9, 2004.

(51) Int. Cl.
*C07D 241/04* (2006.01)
*C07D 295/00* (2006.01)

(52) U.S. Cl. ..................................... 544/358

(58) Field of Classification Search ....................... None
See application file for complete search history.

(56) References Cited

U.S. PATENT DOCUMENTS

| | | | |
|---|---|---|---|
| 3,135,794 A | 6/1964 | Archer | |
| 4,791,104 A | 12/1988 | Picciola et al. | |
| 5,023,265 A | 6/1991 | Scherlock et al. | |
| 5,124,327 A | 6/1992 | Greenlee et al. | |
| 5,192,770 A | 3/1993 | Clark et al. | |
| 5,413,999 A | 5/1995 | Vacca et al. | |
| 5,424,329 A | 6/1995 | Boschelli et al. | |
| 5,811,432 A | 9/1998 | Marfat et al. | |
| 6,008,231 A | 12/1999 | Lebaut et al. | |
| 6,172,085 B1 | 1/2001 | Ohkawa et al. | |
| 6,232,327 B1 | 5/2001 | Nickel et al. | |
| 6,469,006 B1 | 10/2002 | Blair et al. | |
| 6,476,034 B2 | 11/2002 | Wang et al. | |
| 6,573,262 B2 | 6/2003 | Wallace et al. | |
| 6,632,819 B1 | 10/2003 | Wang et al. | |
| 6,825,201 B2 | 11/2004 | Wang et al. | |
| 6,900,206 B2 | 5/2005 | Kadow et al. | |
| 7,037,913 B2 | 5/2006 | Wang et al. | |
| 7,087,610 B2 | 8/2006 | Wang et al. | |
| 7,183,284 B2 | 2/2007 | Kadow et al. | |
| 7,348,337 B2 | 3/2008 | Wang et al. | |
| 7,354,924 B2 | 4/2008 | Wang et al. | |
| 7,396,830 B2 | 7/2008 | Wang et al. | |
| 7,449,476 B2 | 11/2008 | Ruediger et al. | |
| 7,501,419 B2 | 3/2009 | Bachand et al. | |
| 7,504,399 B2 | 3/2009 | Wang et al. | |
| 7,572,810 B2 | 8/2009 | Wang et al. | |
| 2002/0061892 A1 | 5/2002 | Wang et al. | |
| 2003/0069266 A1 | 4/2003 | Wang et al. | |
| 2003/0207910 A1 | 11/2003 | Wang et al. | |
| 2003/0236277 A1 | 12/2003 | Kadow et al. | |
| 2004/0063744 A1 | 4/2004 | Wang et al. | |
| 2004/0063746 A1 | 4/2004 | Regueiro-Ren et al. | |
| 2004/0110785 A1 | 6/2004 | Wang et al. | |
| 2005/0075364 A1 | 4/2005 | Yeung et al. | |
| 2005/0124623 A1 | 6/2005 | Bender et al. | |
| 2005/0209246 A1 | 9/2005 | Ueda et al. | |
| 2005/0215543 A1 | 9/2005 | Lin et al. | |
| 2005/0215544 A1 | 9/2005 | Lin et al. | |
| 2005/0215545 A1 | 9/2005 | Lin et al. | |
| 2006/0100209 A1 | 5/2006 | Gu et al. | |
| 2006/0100432 A1 | 5/2006 | Matiskella et al. | |
| 2007/0249579 A1 | 10/2007 | Wang et al. | |

FOREIGN PATENT DOCUMENTS

| | | |
|---|---|---|
| EP | 0379314 A1 | 7/1990 |
| EP | 0484071 A2 | 5/1992 |
| EP | 0530907 A1 | 3/1993 |
| EP | 1069111 A1 | 1/2001 |
| WO | WO 93/01181 | 1/1993 |
| WO | WO 95/04742 | 2/1995 |
| WO | WO 96/11929 | 4/1996 |
| WO | WO 97/24350 | 7/1997 |
| WO | WO 98/28292 | 7/1998 |
| WO | WO 99/24065 | 5/1999 |
| WO | WO 00/00201 | 1/2000 |
| WO | WO 00/12074 | 3/2000 |
| WO | WO 00/51984 | 9/2000 |
| WO | WO 00/71535 | 11/2000 |

(Continued)

OTHER PUBLICATIONS

Heimbach, et al, "Absorption Rate Limit Considerations for Oral Phosphate Prodrugs," Pharmaceutical Research, 20(6), pp. 848-856, 2003.

(Continued)

*Primary Examiner*—James O Wilson
*Assistant Examiner*—Noble Jarrell
(74) *Attorney, Agent, or Firm*—John F. Levis

(57) ABSTRACT

The instant invention provides crystalline materials of 1-(4-benzoyl-piperazin-1-yl)-2-[4-methoxy-7-(3-methyl-[1,2,4]triazol-1-yl)-1H-pyrrolo[2,3-c]pyridin-3-yl]-ethane-1,2-dione; processes for the production of such crystalline materials; pharmaceutical compositions comprising such crystalline materials; and methods of treating HIV or AIDS with such crystalline materials or such pharmaceutical compositions.

6 Claims, 12 Drawing Sheets

FOREIGN PATENT DOCUMENTS

| WO | WO 00/76521 A1 | 12/2000 |
| WO | WO 01/22954 A2 | 4/2001 |
| WO | WO 01/62255 | 8/2001 |
| WO | WO 02/04440 | 1/2002 |
| WO | WO 02/10152 A2 | 2/2002 |
| WO | WO 02/62423 | 8/2002 |
| WO | WO 02/085301 A2 | 10/2002 |
| WO | WO 03/041644 | 5/2003 |
| WO | WO 03/068221 A1 | 8/2003 |
| WO | WO 03/082881 A | 10/2003 |
| WO | WO 03/092695 | 11/2003 |
| WO | WO 03/103607 | 12/2003 |
| WO | WO 04/000210 A2 | 12/2003 |
| WO | WO 2004/011425 A2 | 2/2004 |
| WO | WO 2004/043337 A2 | 5/2004 |
| WO | WO 2005/016344 | 2/2005 |
| WO | WO 2005/121094 | 12/2005 |

OTHER PUBLICATIONS

Stella, et al, Pharmacokinetics of Drug Targeting: Specific Implications for Targeting Via Prodrugs, Handbook of Experimental Pharmacology, Chapter 4, pp. 71-103, 1991.

Zhu, et al, "A One-Pot Synthesis of Nitrogen-Containing Heteroaryl α-Keto Amides from Heteroaryl Halides," Tetrahedron Letters, 46(20), pp. 3587-3589, 2005.

Yin, et al., "Simulated PXRD Patterns in Studies of the Phase Composition and Thermal Behavior of Bulk Crystalline Solids," American Pharmaceutical Review, 2003, 6, 2, pp. 80-85.

Hotoda, "Small-Molecule Inhibitors of HIV-1 Entry Via Chemokine Receptors," Drugs of the Future, 24(12), pp. 1355-1362, 1999.

Sodroski, "HIV-1 Entry Inhibitors in the Side Pocket," Cell, 9, pp. 243-246, 1999.

Blair, et al, "HIV-1 Entry-An Expanding Portal for Drug Discovery," Drug Discovery Today, 5(5), pp. 183-194, 2000.

Font, et al, "Indoles and Pyridazinol[4,5-b]Indoles as Nonnucleoside Analog Inhibitors of HIV-1 Reverse Transcriptase," Eur. J. Med. Chem., 30, pp. 963-971, 1995.

Romero, et al, J. Med. Chem., 36, pp. 1505-1508, 1993.

Young, et al, "2-Heterocyclic Indole-3-Sulfones as Inhibitors of HIV-1 Reverse Transcriptase," Bioorg. Med. Chem. Lett., 5(5), pp. 491-496, 1995.

Genin, et al, "Synthesis and Bioactivity of Novel Bis(Heteroaryl)Piperazine (BHAP) Reverse Transcriptase Inhibitors: Structure-Activity Relationships and Increased Metabolic Stability of Novel Substituted Pyridine Analogs," J. Med. Chem., 39, pp. 5267-5275, 1996.

Silvestri, et al, Antiviral Chem. Chemother., 9, pp. 139-148, 1998.

Fredenhagen, et al, "Semicochliodinol A and B: Inhibitors of HIV-1 Protease and EGF-R Protein Tyrosine Kinase Related to Asterriquinones Produced by the Fungus Chrysosporium Merdarium," J. of Antibiotics, 50, pp. 395-401, 1997.

Wang, et al., Org. Biol. Chem., 2005, 3, pp. 1781-1786.

Meanwelt et al., Current Opinion in Drug Discovery and Development, 2003, 6, 4, pp. 451-461.

Dueweke, et al, "The Binding of a Novel Bisheteroarylpiperazine Mediates Inhibition of Human Immunodeficiency Virus Type 1 Reverse Transcriptase," J. Biol. Chem., 267(1), pp. 27-30, 1992.

Dueweke, et al, "U-90152, a Potent Inhibitor of Human Immunodeficiency Virus Type 1 Replication," Antimicrob. Agent, Chemother., 37(5), pp. 1127-1131, 1993.

Kato, et al, "New 5-HT$_3$ (Serotonin-3) Receptor Antagonists. IV. Synthesis and Structure-Activity Relationships of Azabicycloalkaneacetamide Derivatives," Chem. Pharm. Bull., 43(8), pp. 1351-1357, 1995.

Levacher, et al, "Broadening in the Scope of NADH Models by Using Chiral and Non Chiral Pyrroto [2,3-b]Pyridine Derivatives," Tetrahedron, 47(3), pp. 429-440, 1991.

Resnyanskaya, et al, "A Simple Synthesis of 1-Acyl-3-Aryl-3H-Pyrrolo[2',3':4,5]Pyrimido[6,1-b]Benzothiazol-6-ium-2-olates: Betainic Derivates of a Novel Heterocyclic System," Synthesis, 18, pp. 2717-2724, 2002.

CRYSTALLINE MATERIALS OF 1-(4-BENZOYL-PIPERAZIN-1-YL)-2-[4-METHOXY-7-(3-METHYL-[1,2,4]TRIAZOL-1-YL)-1H-PYRROLO[2,3-C]PYRIDINE-3-YL]-ETHANE-1,2-DIONE

CROSS-REFERENCE TO RELATED APPLICATIONS

This Continuation application claims the benefit of U.S. Ser. No. 11/267,440 filed Nov. 4, 2005, now pending, which in turn claims the benefit of U.S. Provisional Application Ser. No. 60/626,148 filed Nov. 9, 2004, now expired.

FIELD OF THE INVENTION

The present invention relates to crystalline materials of 1-(4-benzoyl-piperazin-1-yl)-2-[4-methoxy-7-(3-methyl-[1,2,4]triazol-1-yl)-1H-pyrrolo[2,3-c]pyridin-3-yl]-ethane-1,2-dione; processes for the production thereof, pharmaceutical compositions thereof, and methods of treating HIV and AIDS therewith.

BACKGROUND OF THE INVENTION

HIV-1 (human immunodeficiency virus-1) infection remains a major medical problem, with an estimated 42 million people infected worldwide at the end of 2002. The number of cases of HIV and AIDS (acquired immunodeficiency syndrome) has risen rapidly. In 2002, ~5.0 million new infections were reported, and 3.1 million people died from AIDS. Currently available drugs for the treatment of HIV include nine nucleoside reverse transcriptase (RT) inhibitors or approved single pill combinations (zidovudine or AZT (or Retrovir®), didanosine (or Videx®), stavudine (or Zerit®), lamivudine (or 3TC or Epivir®), zalcitabine (or DDC or Hivid®), abacavir succinate (or Ziagen®), Tenofovir disoproxil fumarate salt (or Viread®), Combivir® (contains-3TC plus AZT), Trizivir® (contains abacavir, lamivudine, and zidovudine); three non-nucleoside reverse transcriptase inhibitors: nevirapine (or Viramune®), delavirdine (or Rescriptor®) and efavirenz (or Sustiva®), and eight peptidomimetic protease inhibitors or approved formulations: saquinavir, indinavir, ritonavir, nelfinavir, amprenavir, lopinavir, Kaletra® (lopinavir and Ritonavir), and Atazanavir (Reyataz®). Each of these drugs can only transiently restrain viral replication if used alone. However, when used in combination, these drugs have a profound effect on viremia and disease progression. In fact, significant reductions in death rates among AIDS patients have been recently documented as a consequence of the widespread application of combination therapy. However, despite these impressive results, 30 to 50% of patients ultimately fail combination drug therapies. Insufficient drug potency, non-compliance, restricted tissue penetration and drug-specific limitations within certain cell types (e.g. most nucleoside analogs cannot be phosphorylated in resting cells) may account for the incomplete suppression of sensitive viruses. Furthermore, the high replication rate and rapid turnover of HIV-1 combined with the frequent incorporation of mutations, leads to the appearance of drug-resistant variants and treatment failures when sub-optimal drug concentrations are present (Larder and Kemp; Gulick; Kuritzkes; Morris-Jones et al; Schinazi et al; Vacca and Condra; Flexner; Berkhout and Ren et al; (Ref. 6-14)). Therefore, novel anti-HIV agents exhibiting distinct resistance patterns, and favorable pharmacokinetic as well as safety profiles are needed to provide more treatment options.

U.S. patent application Ser. Nos. 10/038,306 (filed Jan. 2, 2002), 10/214,982 (filed Aug. 7, 2002), and 10/630,278 (filed Jul. 30, 2003) (all of which are herein incorporated by reference) disclose azaindoleoxoacetic piperazine derivatives and compositions that possess antiviral activity and are useful for the treatment of HIV and AIDS. U.S. patent application Ser. No. 10/630,278 discloses the compound 1-(4-benzoyl-piperazin-1-yl)-2-[4-methoxy-7-(3-methyl-[1,2,4]triazol-1-yl)-1H-pyrrolo[2,3-c]pyridin-3-yl]-ethane-1,2-dione, which has the chemical structure (I) (Compound (I)):

Compound (I)

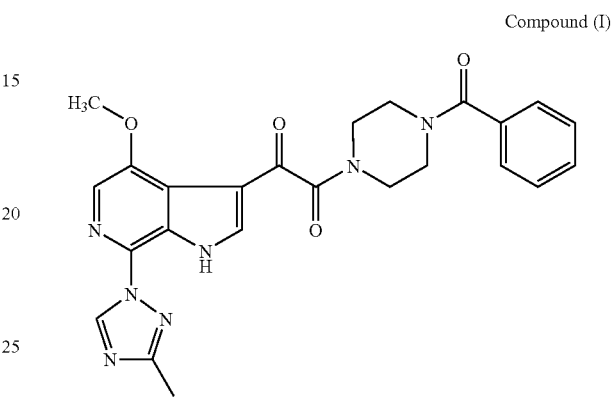

U.S. patent application Ser. No. 10/630,278 also discloses that Compound (I) can be prepared according to the following scheme:

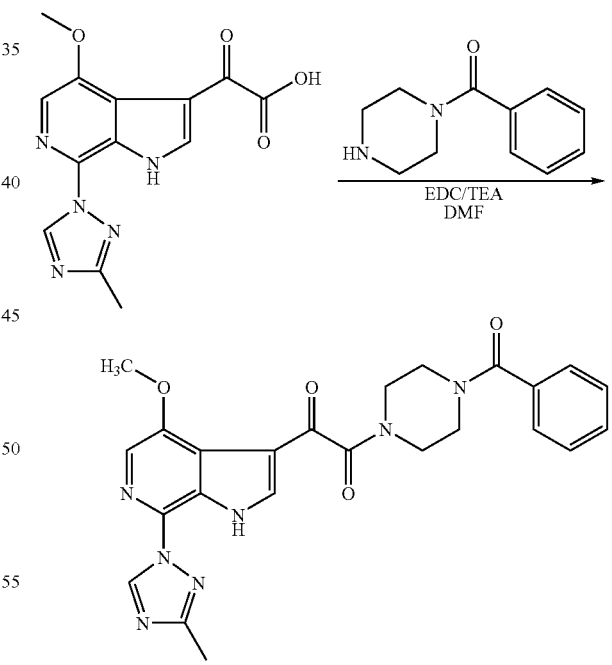

This reaction can also be performed by use of HATU and DMAP to provide more consistent yield of the title compound.

There exists a need for different forms of Compound (I), since different forms of Compound (I) have different physical and chemical properties. There is also a need to produce a stable form of Compound (I) for long term storage etc. There is also a need for reliable and reproducible methods for the manufacture, purification, and formulation of Compound (I) to permit its feasible commercialization.

These and other aspects of the invention will become more apparent from the following detailed description.

SUMMARY OF THE INVENTION

The present invention relates to several different crystalline materials of Compound (I) (1-(4-benzoyl-piperazin-1-yl)-2-[4-methoxy-7-(3-methyl-[1,2,4]triazol-1-yl)-1H-pyrrolo[2,3-c]pyridin-3-yl]-ethane-1,2-dione). Each material exhibits distinct chemical and physical properties. The present invention also relates to stable, reliable and reproducible methods for the manufacture, purification, and formulation of Compound (I) to permit its feasible commercialization. The present invention is directed to these, as well as other important aspects.

These and other aspects of the invention will become more apparent from the following detailed description.

BRIEF DESCRIPTION OF THE FIGURES

The invention is illustrated by reference to the accompanying drawings described below.

DETAILED DESCRIPTION OF THE INVENTION

Figure 1:
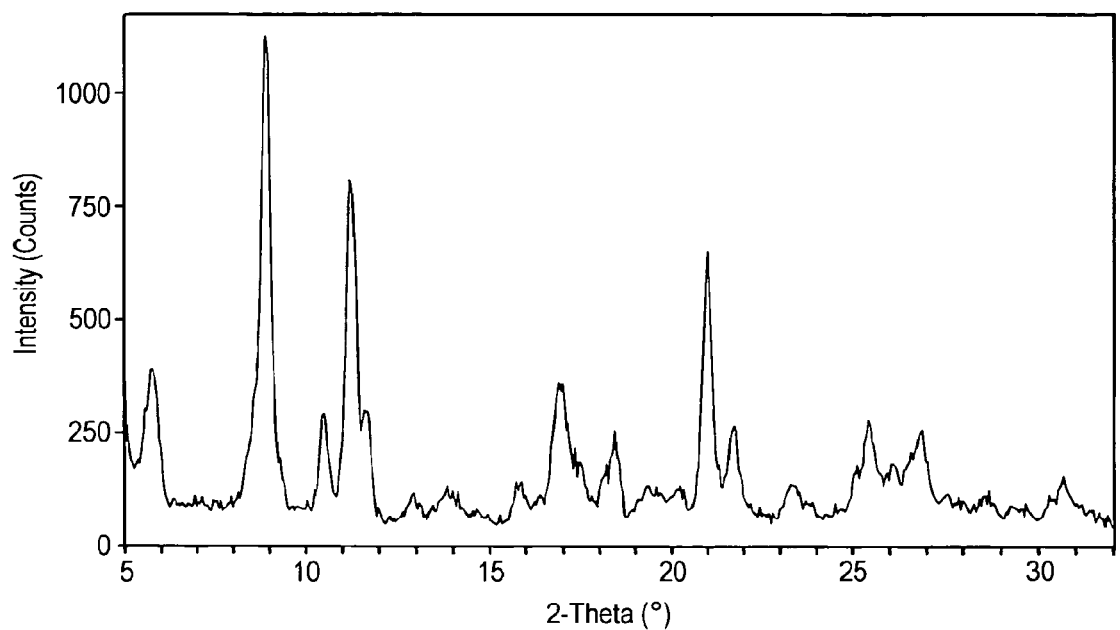
FIG. 1. XRPD pattern of crystalline material Form P-1 of Compound (I).

The present invention provides, at least in part, crystalline materials of Compound (I), including crystalline forms of solvates of Compound (I), as a novel material, in particular in pharmaceutically acceptable form. The term "pharmaceutically acceptable", as used herein, refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio. In certain preferred embodiments, Compound (I) or each of its solvates is in substantially pure form. The term "substantially pure", as used herein, means a compound having a corrected purity greater than about 90% including, for example, about 91%, about 92%, about 93%, about 94%, about 95%, about 96%, about 97%, about 98%, about 99%, and about 100%.

Compound (I) may be prepared using methods well known to the skilled artisan of organic synthesis, as well as methods taught in commonly assigned application Publication Ser. No. 10/630,278 (filed Jul. 30, 2003), and concurrently filed applications, the disclosures of which are hereby incorporated herein by reference, in their entireties.

Generally speaking, the crystalline materials of Compound (I) may be prepared by a variety of methods, including but not limited to, recrystallizing Compound (I), preferably in a neat form, from a suitable solvent. More preferably, the crystalline form of Compound (I) is obtained directly from a reaction mixture through the addition of a suitable solvent. In certain preferred embodiments, Compound (I) is obtained through either recrystallization or solvent addition using a solvent which is to be incorporated in the solvate. Suitable solvents include those mentioned above in connection with the solvates.

Procedures for recrystallization of the preferred crystalline forms of Compound (I) and its solvates will be readily understood by one skilled in the art, once placed in possession of the present disclosure. By way of general guidance, Compound (I) may be suspended and/or stirred in a suitable solvent to afford a slurry, which may be heated to promote dissolution. The term "slurry", as used herein, means a saturated solution of Compound (I), which may also contain an additional amount of Compound (I) to afford a heterogeneous mixture of Compound (I) and a solvent at a given temperature. Suitable solvents in this regard include, for example, polar aprotic solvents, polar protic solvents, and mixtures of two or more of these.

Suitable polar aprotic solvents include, for example, acetone, methyl ethyl ketone (MEK), dimethylformamide (DMF), dimethylacetamide (DMAC), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile (ACN), dimethylsulfoxide (DMSO), propionitrile, ethyl formate, methyl acetate, ethyl acetate, isopropyl acetate (IpOAc), butyl acetate (BuOAc), t-butyl acetate, hexachloroacetone, dioxane, sulfolane, N,N-dimethylpropionamide, nitromethane, nitrobenzene and hexamethylphosphoramide.

Suitable polar protic solvents include, for example, alcohols and glycols, such as methanol, ethanol, 1-propanol, 2-propanol, isopropanol (IPA), 1-butanol (1-BuOH), 2-butanol (2-BuOH), i-butyl alcohol, t-butyl alcohol, 2-nitroethanol, 2-fluoroethanol, 2,2,2-trifluoroethanol, ethylene glycol, 2-methoxyethanol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, glycerol and methyl t-butyl ether (MTBE).

Preferred solvents include, for example, acetone, ACN, DMSO, DMF, NMP, MEK, 2-BuOH, IPA, IpOAc, MTBE, and BuOAc.

Other solvents suitable for the preparation of slurries of Compound (I), in addition to those exemplified above, would be apparent to one skilled in the art, based on the present disclosure.

Seed crystals may be added to any crystallization mixture to promote crystallization. As will be clear to the skilled artisan, seeding is used as a means of controlling growth of a particular polymorph or as a means of controlling the particle size distribution of the crystalline product. Accordingly, calculation of the amount of seeds needed depends on the size of the seed available and the desired size of an average product particle as described, for example, in "Programmed cooling of batch crystallizers," J. W. Mullin and J. Nyvlt, *Chemical Engineering Science*, 1971, 26, 369-377. In general, seeds of small size are needed to effectively control the growth of crystals in the batch. Seeds of small size may be generated by sieving, milling, or micronizing of larger crystals, or by micro-crystallization of solutions. Care should be taken that milling or micronizing of crystals does not result in any change in crystallinity from the desired crystalline form (i.e. change to amorphous or to another polymorph).

The cooled mixture may be filtered under vacuum, and the isolated solids may be washed with a suitable solvent, such as cold re-crystallization solvent, and dried under a nitrogen purge to afford the desired crystalline form. The isolated solids may be analyzed by a suitable spectroscopic or analytical technique, such as SSNMR, DSC, XRPD, or the like, to assure formation of the preferred crystalline form of the product. The resulting crystalline form is typically produced in an amount of greater than about 70% isolated yield, but preferably greater than 90% based on the amount of Compound (I) originally employed in the crystallization procedure. The product may be co-milled or passed through a mesh screen to delump the product, if necessary.

Preferred crystalline forms may also be prepared directly from the reaction medium of the final process step for preparing Compound (I). This may be achieved, for example, by employing in the final process step a solvent or mixture of solvents from which Compound (I) may be crystallized. Alternatively, preferred crystalline forms may be obtained by distillation or solvent addition techniques which would be apparent to the skilled artisan, once placed in possession of the present disclosure. Preferably, such techniques may be carried out following the final process step for preparing Compound (I) through the addition of a solvent suitable for isolating the product in crystalline form. Suitable solvents for this purpose include any of those solvents described herein.

By way of general guidance, the reaction mixture may be filtered to remove any undesired impurities, inorganic salts, and the like, followed by washing with reaction or crystallization solvent. The resulting solution may be concentrated to remove excess solvent or gaseous constituents. If distillation is employed, the ultimate amount of distillate collected may vary, depending on process factors including, for example, vessel size, stirring capability, and the like, by way of general guidance, the reaction solution may be distilled to about {fraction (1/10)} the original volume before solvent replacement is carried out. The reaction may be sampled and assayed to determine the extent of the reaction and the wt % product in accordance with standard process techniques. If desired, additional reaction solvent may be added or removed to optimize reaction concentration. Preferably, the final concentration is adjusted to about 50 wt % at which point a slurry typically results.

It may be preferable to add solvents directly to the reaction vessel without distilling the reaction mixture. Preferred solvents for this purpose are those which may ultimately participate in the crystalline lattice as discussed above in connection with solvent exchange. Although the final concentration may vary depending on desired purity, recovery and the like, the final concentration of Compound (I) in solution is preferably about 4% to about 7%. The reaction mixture may be stirred following solvent addition and simultaneously warmed. By way of illustration, the reaction mixture may be stirred for about 1 hour while warming to about 70° C. The reaction is preferably filtered hot and washed with either the reaction solvent, the solvent added or a combination thereof. Seed crystals may be added to any crystallization solution to initiate crystallization.

The various forms described herein may be distinguishable from one another through the use of various analytical techniques known to one of ordinary skill in the art. Such techniques include, but are not limited to, X-ray powder diffraction (XRPD), differential scanning calorimetry (DSC), and/or thermogravimetric analysis (TGA).

X-Ray Powder Diffraction (XRPD)

One of ordinary skill in the art will appreciate that an X-ray diffraction pattern may be obtained with a measurement error that is dependent upon the measurement conditions employed. In particular, it is generally known that intensities in a X-ray diffraction pattern may fluctuate depending upon measurement conditions employed. It should be further understood that relative intensities may also vary depending upon experimental conditions and, accordingly, the exact order of intensity should not be taken into account. Additionally, a measurement error of diffraction angle for a conventional X-ray diffraction pattern is typically about 5% or less, and such degree of measurement error should be taken into account as pertaining to the aforementioned diffraction angles. Consequently, it is to be understood that the crystal forms of the instant invention are not limited to the crystal forms that provide X-ray diffraction patterns completely identical to the X-ray diffraction patterns depicted in the accompanying Figures disclosed herein. Any crystal forms that provide X-ray diffraction patterns substantially identical to those disclosed in the accompanying Figures fall within the scope of the present invention. The ability to ascertain substantial identities of X-ray diffraction patterns is within the purview of one of ordinary skill in the art.

X-Ray powder diffraction data for the crystalline forms of Compound (I) were obtained using a Rigaku miniflex X-ray diffractometer, Bruker D8 Advance X-ray diffectometer, or Bruker D8 Discover (GADDS) X-ray diffractometer. The radiation was CuKα. Data were typically collected at room temperature for the range of 3-35°. Powder samples were packed in glass capillaries when GADDS was used for data collection, and the capillary was rotated during data collection. The resulting two-dimensional diffraction arcs were integrated to create a traditional 1-dimensional XRPD pattern with a step size of 0.02°.

Differential Scanning Calorimetry (DSC)

The DSC instrument used to test the crystalline forms was a TA Instruments® Differential Scanning Calorimetry Model 2910, TA Instruments® Modulated Differential Scanning Calorimetry Model 2920, or TA Instruments® Modulated Differential Scanning Calorimetry Model Q1000. The DSC cell/sample chamber was purged with 100 ml/min of ultra-high purity nitrogen gas. The instrument was calibrated with high purity indium. The accuracy of the measured sample temperature with this method is within about +/−1° C., and the heat of fusion can be measured within a relative error of about +/−5%. The sample was placed into an open aluminum DSC pan and measured against an empty reference pan. About 2-6 mg of sample powder was placed into the bottom of the pan and lightly tapped down to make contact with the pan. The weight of the sample was measured accurately and recorded to a hundredth of a milligram. The instrument was programmed to heat at 10° C. per minute in the temperature range between 25 and 300° C.

The heat flow, which was normalized by a sample weight, was plotted versus the measured sample temperature. The data were reported in units of watts/gram ("W/g"). The plot was made with the endothermic peaks pointing down. The endothermic melt peak was evaluated for extrapolated onset temperature, peak temperature, and heat of fusion in this analysis.

Thermogravimetric Analysis (TGA)

The TGA instruments used to test the crystalline forms was a TA Instruments® High Resolution Thermogravimetric Analyzer Q500 or TA Instruments® High Resolution Thermogravimetric Analyzer 2950. Samples of 15 to 20 milligrams were analyzed at a heating rate of 10° C. per minute in the temperature range between 25° C. and about 300° C.

Compound (I) may be present in the novel crystalline forms as the neat form, solvate and/or hydrate. A wide variety of solvents may be employed in the preparation of the solvates of Compound (I). Preferred solvents include, for example, polar solvents, including polar protic and polar aprotic solvents. In preferred form, the solvent employed in the preparation include, for example, DMF or acetone, preferably acetone. The ratio of Compound (I) to solvent in the solvates may vary and depends, for example, on the particular solvent selected and the methods for preparing the solvates. Preferably, the solvates are monosolvates, hemisolvates, non-stoichiometric or disolvates.

Four different crystalline materials, P-1, P-2, P-3, and P-4, were obtained. P-1 is a neat form. P-2, P-3, and P-4 are all solvates.

Table 1 lists some of the solvent system tested in polymorph screening.

Figure 2:
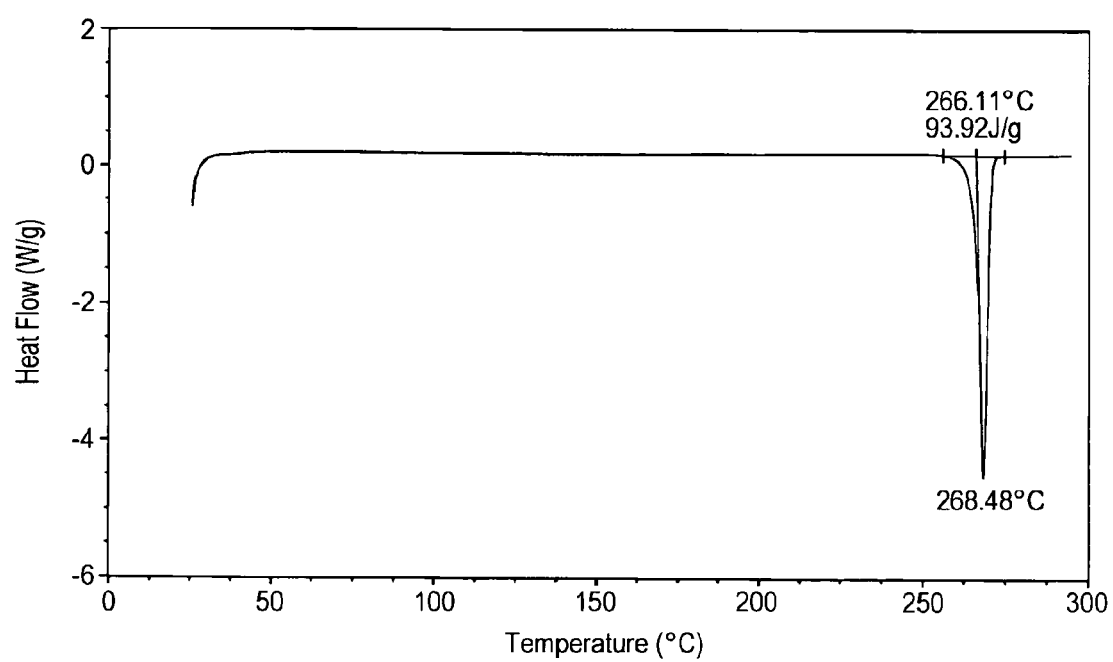
FIG. 2. DSC of crystalline material Form P-1 of Compound (I).
Figure 3:
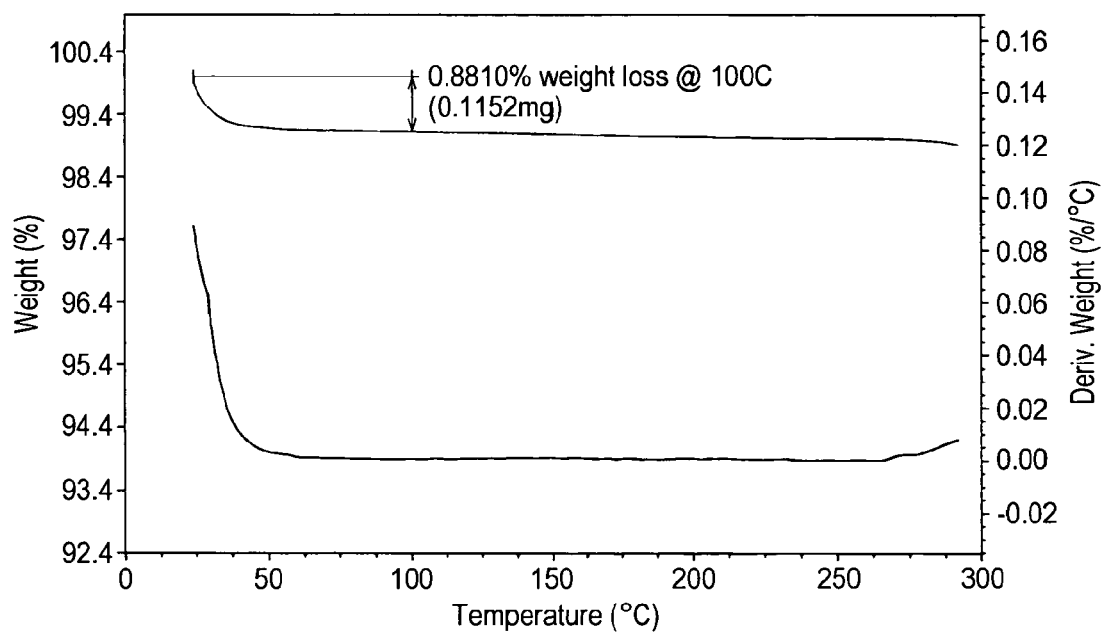
FIG. 3. TGA of crystalline material Form P-1 of Compound (I).

P-1 Form can be prepared by recrystallization from various solvents, such as acetone, methanol, dichloromethane, or acetic acid, as described in Table 1. Form P-1 has a melting point of ~266±10° C. Suspension of P-1 form in various solvents at room temperature or elevated temperature did not show any phase conversion, suggesting that P-1 is a pure and stable form. The XRPD pattern of P-1 form is shown in FIG. 1, comprising peaks selected from the group at 2θ=8.90±0.10, 11.21±0.10, 16.91±0.10 and 21.00±0.10°. DSC thermogram of Form P-1 is provided in FIG. 2, which has an endothermic peak at about 268° C. TGA of Form P-1 is provided in FIG. 3, which showed no significant weight loss up to 250° C. The physicochemical properties of Form P-1 of Compound (I) are summarized in Table. Form P-1 is crystalline with low hygroscopicity. The aqueous solubility of P-1 is pH dependent with an intrinsic solubility of 0.0027 mg/mL at room temperature at pH 5.7. The aqueous solubility increases to 0.25 mg/mL at pH 10.1. It shows acceptable solid-state stability as shown in Table 3. No significant change in potency or in total impurity content was observed when exposed to stress temperature/humidity conditions for 4 weeks. However, it is light sensitive as it exhibited an increase of total impurity to 0.3% upon exposure to high-intensity visible/UV light for 2 weeks.

TABLE 1

Polymorph screening using recrystallization from solvents and solvent mediated polymorphic transformation methods

| Methods | Solvents used |
| --- | --- |
| Recrystallization by Cooling[1] | acetic acid (50° C.), acetone (50° C.), acetonitrile (70° C.), dichloromethane (50° C.), ethyl acetate (65° C.), methanol (50° C.), nitromethane (75° C.), tetrahydrofuran (65° C.), dimethylformamide/water (2:1)[2] (75° C.) |
| Solvent mediated polymorphic transformation[3] | acetone, acetonitrile, dichloromethane, ethyl acetate, isopropyl alcohol, methanol, tetrahydrofuran, toluene, acetonitrile/water (1:1)[2], methanol/water (1:1)[2], water (40° C.) |

[1]A saturated solution was prepared at fixed temperature indicated in the parentheses and was cooled to 20° C. over an hour. Both wet and dried crystals were collected for characterization.
[2]Volume ratio of solvents
[3]Excess solids (P-I crystals) were suspended in various solvents or solvent mixtures for 7 days at the room temperature. The solids were also suspended in acetonitrile, ethyl acetate and methanol at 60° C. for 3 days and in water at 40° C. for 7 days.

TABLE 2

Physicochemical properties of Form P-1

| | |
| --- | --- |
| Aqueous solubility at 25° C. | 0.012 mg/mL (pH 1.4), 0.0027 mg/mL (pH 5.7), 0.014 mg/mL (pH 8.6), 0.25 mg/mL (pH 10.1) |
| pKa | 8.4 |
| Hygroscopicity | Low hygroscopicity (1% weight gain under 30-60% RH and 3.2% maximum water uptake at 90% RH) |
| Partition coefficient (Log $P_{O/W}$) | 1.13 (pH 1.1), 1.58 (pH 4.5), 1.64 (pH 7.4) |

TABLE 3

Solid-state stability of Form P-1

| Condition | Time (weeks) | Purity (As Is) % | Impurity Index (%) |
| --- | --- | --- | --- |
| Initial | — | 100.7 | <0.03 |
| −20° C. - closed | 4 | 99.9 | 0.05 |
| 25° C. HIL/UV - exposed | 2 | 98.3 | 0.3 |
| 25° C. HIL/UV - protected | 2 | 99.9 | <0.03 |
| 25° C./60% RH - closed | 4 | 101.3 | 0.04 |
| 40° C./75% RH - closed | 4 | 96.7 | 0.04 |
| 40° C./75% RH - open | 4 | 99.3 | 0.04 |
| 50° C. - closed | 4 | 100.7 | 0.08 |

Figure 4:
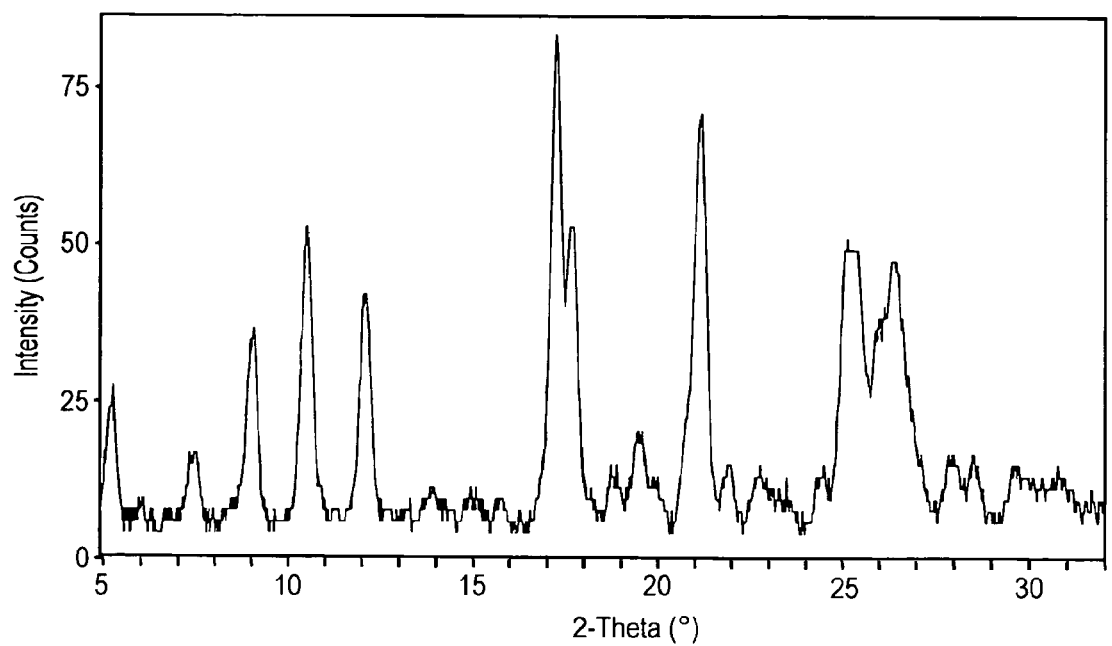
FIG. 4. XRPD pattern of crystalline material Form P-2 of Compound (I).
Figure 5:
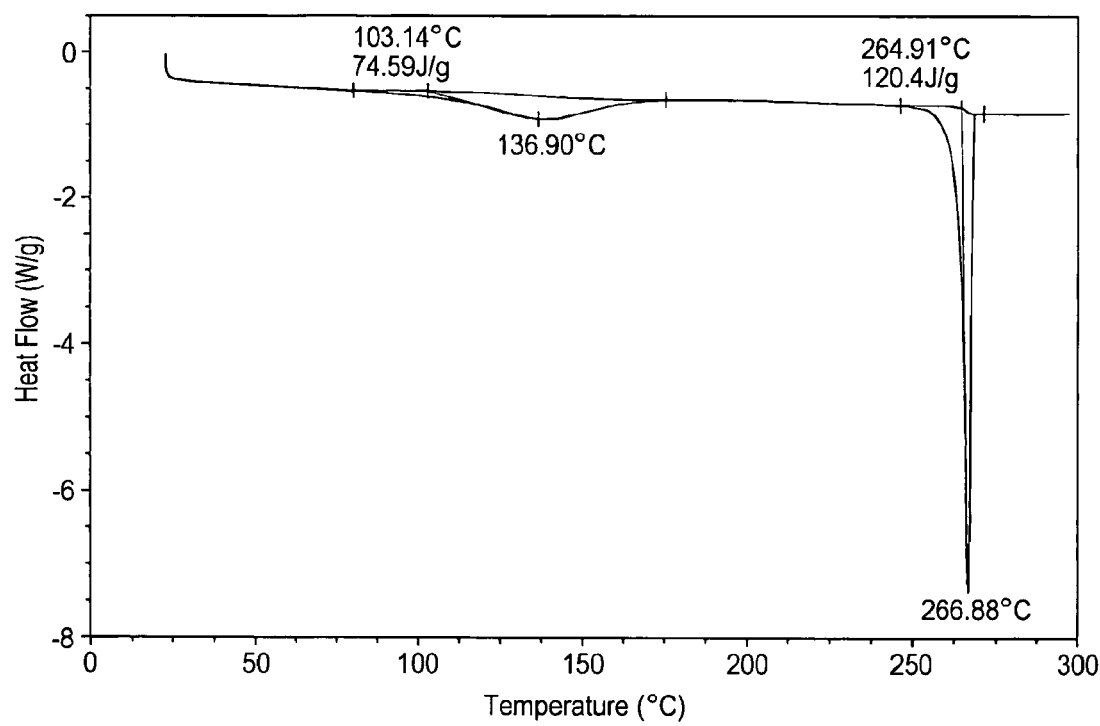
FIG. 5. DSC of crystalline material Form P-2 of Compound (I).
Figure 6:
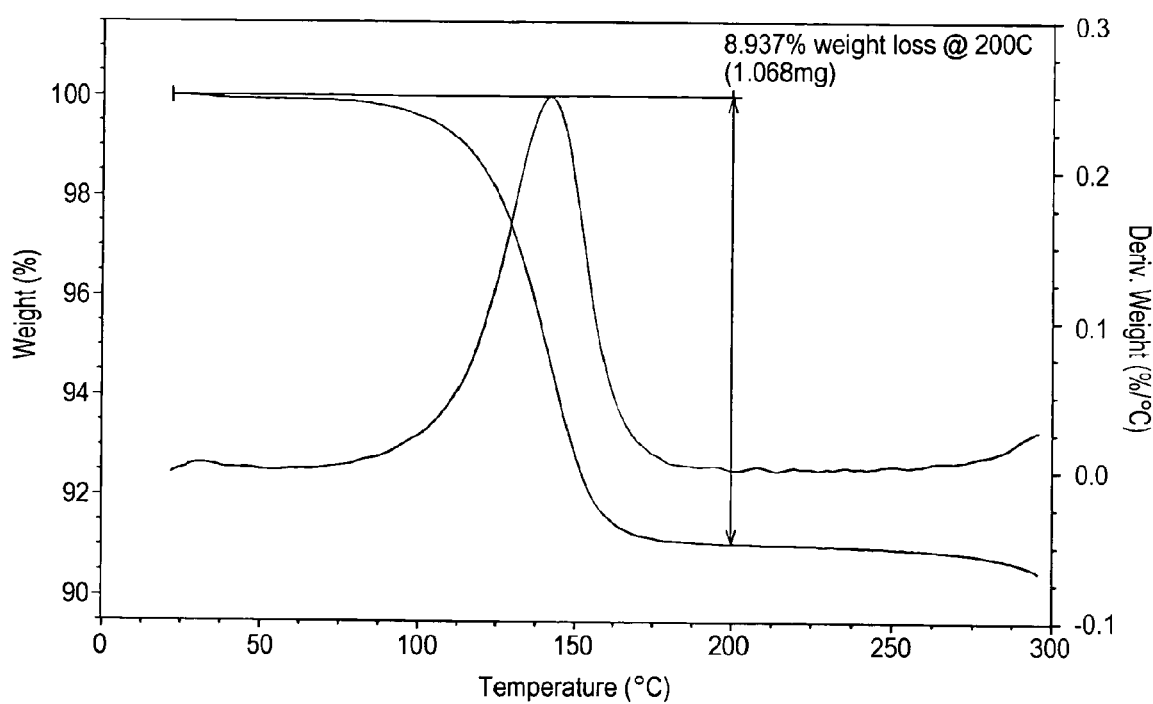
FIG. 6. TGA of crystalline material Form P-2 of Compound (I).

P-2 Form can be prepared by recrystallizing the compound in a variety of solvents (e.g. water, acetonitrile, MeOH) mixed with 1-methyl-2-pyrrolidinone. The XRPD pattern of Form P-2 is shown in FIG. 4, which comprises peaks, selected from the group, at 2θ=5.28±0.10, 9.13±0.10, 10.57±0.10 and 21.31±0.10°. DSC of Form P-2 is provided in FIG. 5, which has an endothermic peak at about 264° C. and an exothermic peak at about 139° C. TGA of Form P-2 is provided in FIG. 6, which showed a significant weight loss of ~27% by ~200° C.

Figure 7:
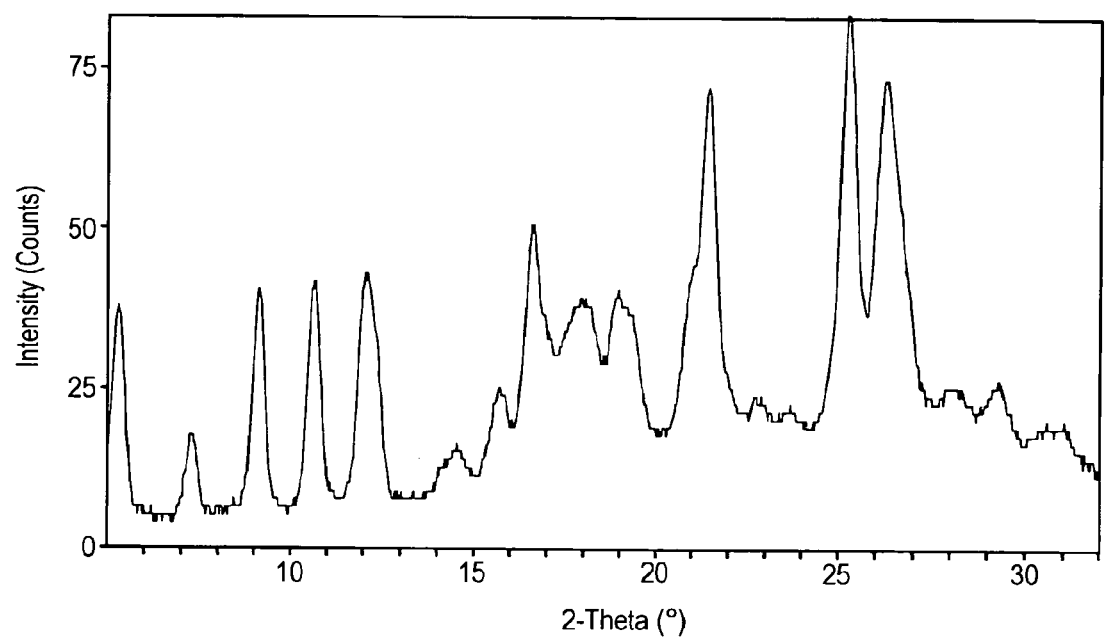
FIG. 7. XRPD pattern of crystalline material Form P-3 of Compound (I).
Figure 8:
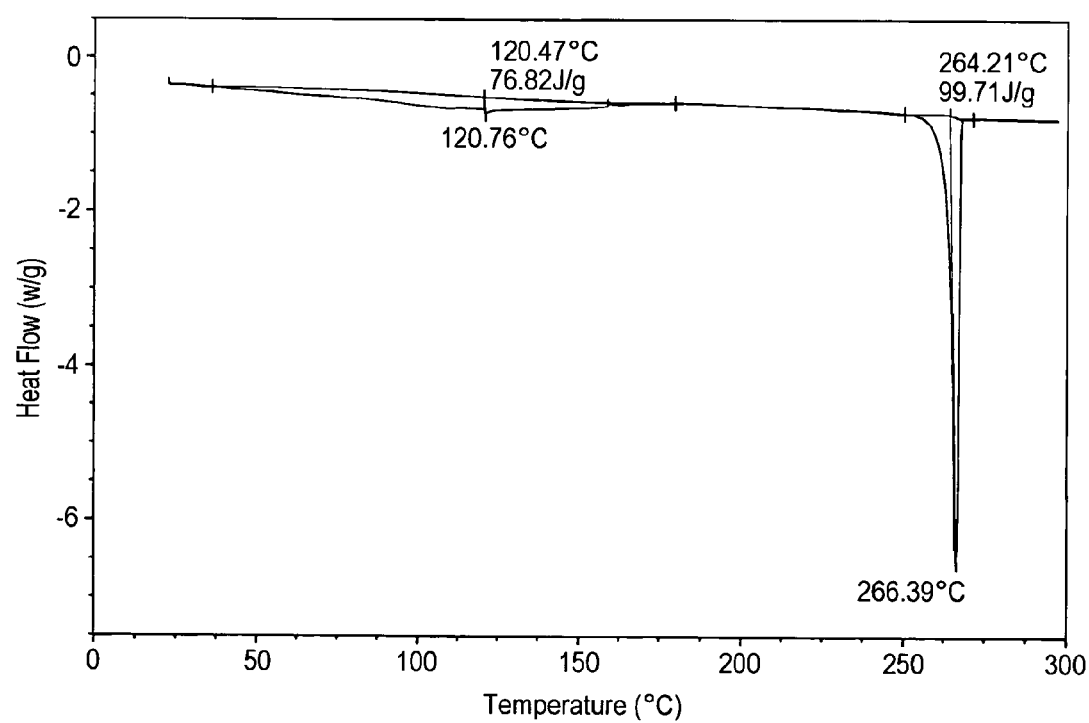
FIG. 8. DSC of crystalline material Form P-3 of Compound (I).
Figure 9:
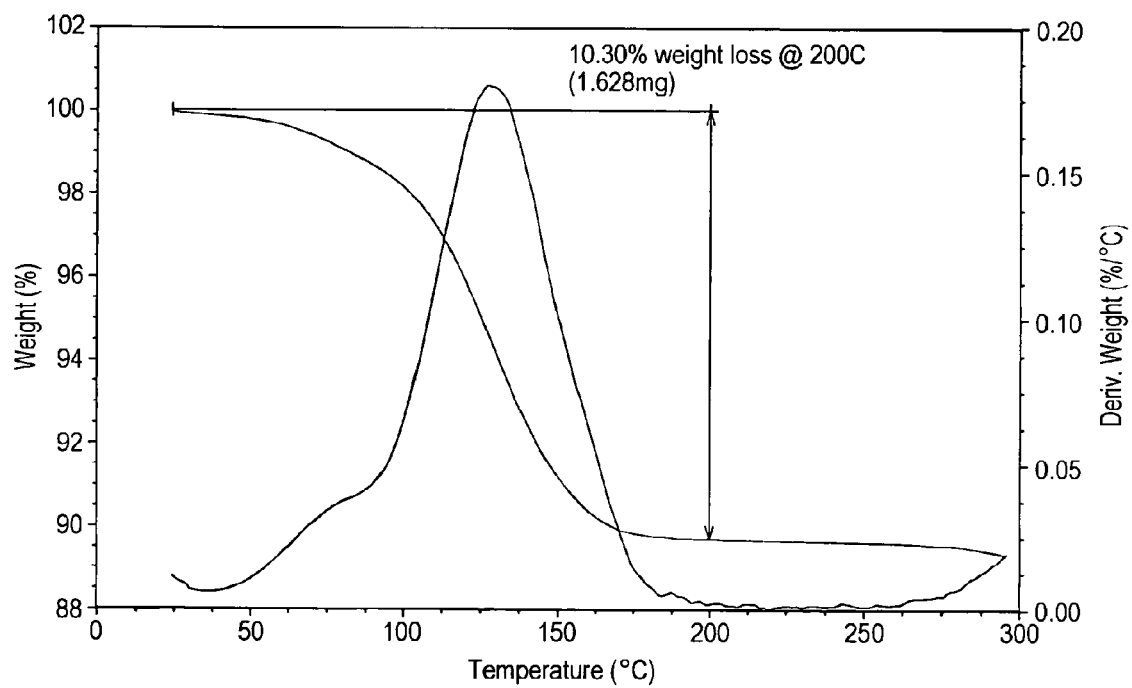
FIG. 9. TGA of crystalline material Form P-3 of Compound (I).

P-3 Form can be prepared by suspending Form P-1 in tetrahydrofuran for a few days (1-7 days) or by recrystallization from tetrahydrofuran. The XRPD pattern of Form P-3 form is shown in FIG. 7, which comprises peaks, selected from the group, at 2θ=10.66±0.10, 12.16±0.10, 21.46±0.10 and 25.28±0.10°. DSC of Form P-3 is provided in FIG. 8, which has two endothermic peaks at about 120° C. and 266° C. respectively. TGA of Form P-3 is provided in FIG. 9, which showed a weight loss of ~1% by ~200° C.

Figure 10:
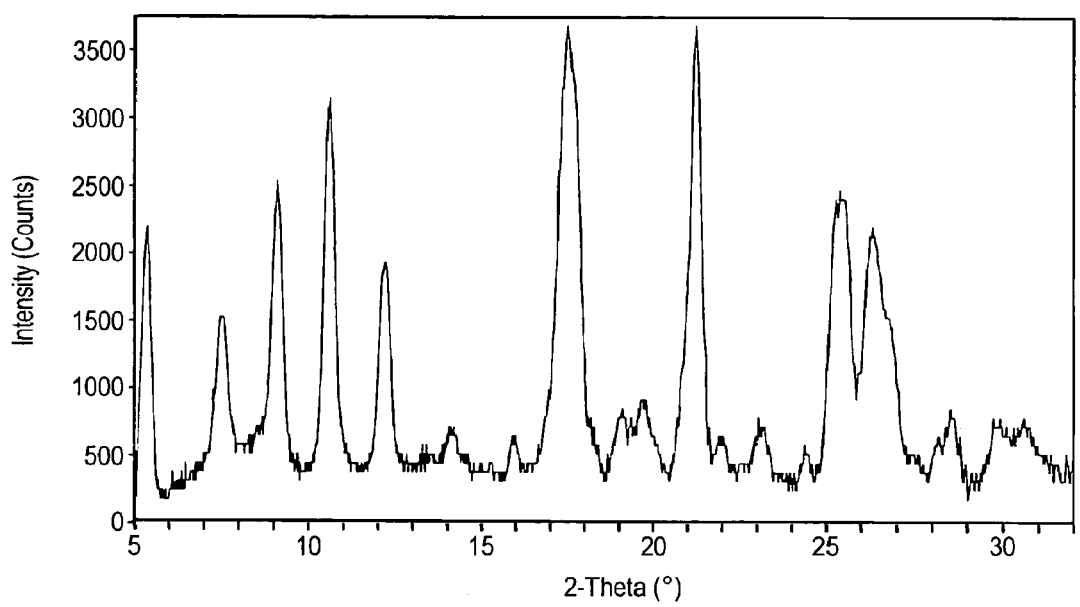
FIG. 10. XRPD pattern of crystalline material Form P-4 of Compound (I).
Figure 11:
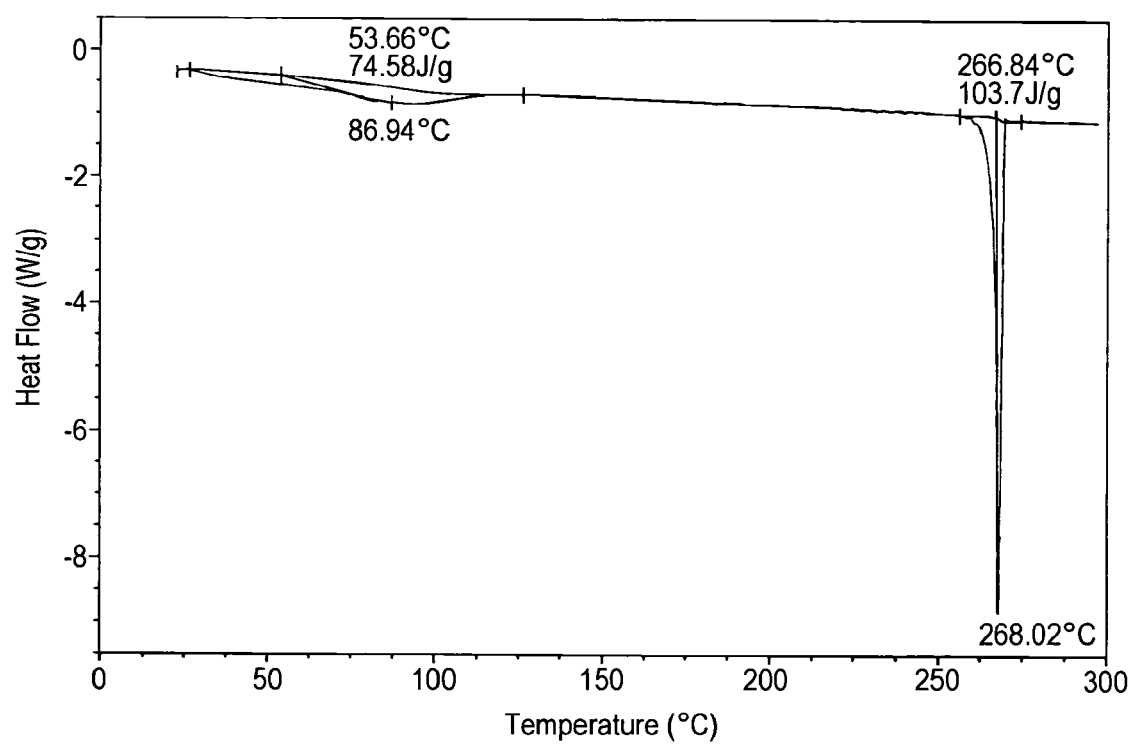
FIG. 11. DSC of crystalline material Form P-4 of Compound (I).

P-4 Form can be prepared by recrystallizing from DMF/water. The XRPD pattern of Form P-4 is shown in FIG. 10, which comprises peaks, selected from the group, at 2θ=9.12±0.10, 10.64±0.10, 17.52±0.10 and 21.28±0.10°. DSC of Form P-4 is provided in FIG. 11, which has two endothermic peaks at about 87° C. and 268° C. respectively.

Figure 12:
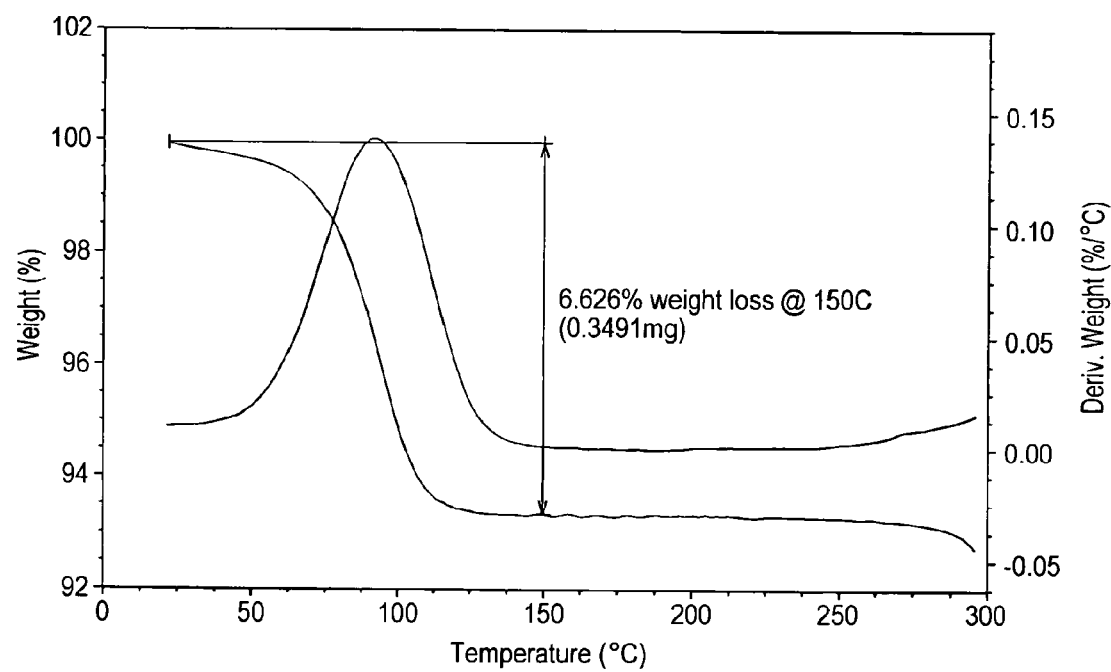
FIG. 12. TGA of crystalline material Form P-4 of Compound (I).

TGA of Form P-4 is provided in FIG. 12 which showed a weight loss of ~7% by ~150° C.

ABBREVIATIONS

The following abbreviations, most of which are conventional abbreviations well known to those skilled in the art, are used throughout the description of the invention and the examples. Some of the abbreviations used are as follows:

h=hour(s)
rt=room temperature
mol=mole(s)
mmol=millimole(s)
g=gram(s)
mg=milligram(s)
mL=milliliter(s)
TFA=Trifluoroacetic Acid
DCE=1,2-Dichloroethane
$CH_2Cl_2$=Dichloromethane
TPAP=tetrapropylammonium perruthenate
THF=Tetrahydrofuran
DEPBT=3-(Diethoxyphosphoryloxy)-1,2,3-benzotriazin-4(3H)-one
DMAP=4-dimethylaminopyridine
P-EDC=Polymer supported 1-(3-dimethylaminopropyl)-3-ethylcarbodiimide
EDC=1-(3-dimethylaminopropyl)-3-ethylcarbodiimide
DMF=N,N-dimethylformamide
Hunig's Base=N,N-Diisopropylethylamine
mCPBA=meta-Chloroperbenzoic Acid
azaindole=1H-Pyrrolo-pyridine
4-azaindole=1H-pyrrolo[3,2-b]pyridine
5-azaindole=1H-Pyrrolo[3,2-c]pyridine
6-azaindole=1H-pyrrolo[2,3-c]pyridine
7-azaindole=1H-Pyrrolo[2,3-b]pyridine
PMB=4-Methoxybenzyl
DDQ=2,3-Dichloro-5,6-dicyano-1,4-benzoquinone
OTf=Trifluoromethanesulfonoxy
NMM=4-Methylmorpholine
PIP-COPh=1-Benzoylpiperazine
NaHMDS=Sodium hexamethyldisilazide
EDAC=1-(3-Dimethylaminopropyl)-3-ethylcarbodiimide
TMS=Trimethylsilyl
DCM=Dichloromethane
DCE=Dichloroethane
MeOH=Methanol
THF=Tetrahydrofuran
EtOAc=Ethyl Acetate
LDA=Lithium diisopropylamide
TMP-Li=2,2,6,6-tetramethylpiperidinyl lithium
DME=Dimethoxyethane
DIBALH=Diisobutylaluminum hydride
HOBT=1-hydroxybenzotriazole
CBZ=Benzyloxycarbonyl
PCC=Pyridinium chlorochromate
Me=Methyl
Ph=Phenyl The crystalline materials of Compound (I) described herein may be formulated into pharmaceutical compositions and/or employed in therapeutic and/or prophylactic methods. These methods include, but are not limited to, the administration of the crystalline compound (I), alone or in combination with one or more other pharmaceutically active agents, including agents that may be useful in the treatment of the disorders mentioned herein.

"Therapeutically effective amount" is intended to include an amount of the crystalline forms of Compound (I) that is effective when administered alone or in combination to treat HIV and AIDS. The crystalline forms of Compound (I) and pharmaceutical compositions thereof may be useful in treating HIV or AIDS. If Compound (I) is used in combination with another medication, the combination of compounds described herein may result in a synergistic combination. Synergy, as described for example by Chou and Talalay, *Adv. Enzyme Regul.* 1984, 22, 27-55, occurs when the effect of the compounds when administered in combination is greater than the additive effect of the compounds when administered alone as a single agent.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

The methods preferably comprise administering to a patient a pharmaceutically effective amount of the novel crystals of the present invention, preferably in combination with one or more pharmaceutically acceptable carriers and/or excipients. The relative proportions of active ingredient and carrier and/or excipient may be determined, for example, by the solubility and chemical nature of the materials, chosen route of administration and standard pharmaceutical practice.

The crystalline forms of Compound (I) may be administered to a patient in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They may be administered alone, but generally will be administered with a pharmaceutical carrier selected on the basis of the chosen route of administration and standard pharmaceutical practice.

The dosage regimen for the crystalline forms of Compound (I) will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder. Obviously, several unit dosage forms may be administered at about the same time. The dosage of the crystalline form of Compound (I) that will be most suitable for prophylaxis or treatment may vary with the form of administration, the particular crystalline form of the compound chosen and the physiological characteristics of the particular patient under treatment. Broadly, small dosages may be used initially and, if necessary, increased by small increments until the desired effect under the circumstances is reached.

By way of general guidance, in the adult, suitable doses may range from about 0.001 to about 1000 mg/Kg body weight, and all combinations and subcombinations of ranges and specific doses therein. Preferred doses may be from about 0.01 to about 100 mg/kg body weight per day by inhalation, preferably 0.1 to 70, more preferably 0.5 to 20 mg/Kg body weight per day by oral administration, and from about 0.01 to about 50, preferably 0.01 to 10 mg/Kg body weight per day by intravenous administration. In each particular case, the doses may be determined in accordance with the factors distinctive to the subject to be treated, such as age, weight, general state of health and other characteristics which can influence the efficacy of the medicinal product. The crystalline forms of Compound (I) may be administered in a single daily dose, or the total daily dosage may be administered in divided doses of two, three, or four times daily.

For oral administration in solid form such as a tablet or capsule, the crystalline forms of Compound (I) can be combined with a non-toxic, pharmaceutically acceptable inert carrier, such as lactose, starch, sucrose, glucose, methylcellulose, magnesium stearate, dicalcium phosphate, calcium sulfate, mannitol, sorbitol and the like.

Preferably, in addition to the active ingredient, solid dosage forms may contain a number of additional ingredients referred to herein as "excipients". These excipients include among others diluents, binders, lubricants, glidants and disintegrants. Coloring agents may also be incorporated. "Diluents", as used herein, are agents which impart bulk to the formulation to make a tablet a practical size for compression. Examples of diluents are lactose and cellulose. "Binders", as used herein, are agents used to impart cohesive qualities to the powered material to help ensure the tablet will remain intact after compression, as well as improving the free-flowing qualities of the powder. Examples of typical binders are lactose, starch and various sugars. "Lubricants", as used herein, have several functions including preventing the adhesion of the tablets to the compression equipment and improving the flow of the granulation prior to compression or encapsulation. Lubricants are in most cases hydrophobic materials. Excessive use of lubricants is undesired, however, as it may result in a formulation with reduced disintegration and/or delayed dissolution of the drug substance. "Glidants", as used herein, refer to substances which may improve the flow characteristics of the granulation material. Examples of glidants include talc and colloidal silicon dioxide. "Disintegrants", as used herein, are substances or a mixture of substances added to a formulation to facilitate the breakup or disintegration of the solid dosage form after administration. Materials that may serve as disintegrants include starches, clays, celluloses, algins, gums and cross-linked polymers. A group of disintegrants referred to as "super-disintegrants" generally are used at a low level in the solid dosage form, typically 1% to 10% by weight relative to the total weight of the dosage unit. Croscarmelose, crospovidone and sodium starch glycolate represent examples of a cross-linked cellulose, a cross-linked polymer and a cross-linked starch, respectively. Sodium starch glycolate swells seven- to twelve-fold in less than 30 seconds effectively disintegrating the granulations that contain it.

The disintegrant preferably used in the present invention is selected from the group comprising modified starches, croscarmallose sodium, carboxymethylcellulose calcium and crospovidone. A more preferred disintegrant in the present invention is a modified starch such as sodium starch glycolate.

Preferred carriers include capsules or compressed tablets which contain the solid pharmaceutical dosage forms described herein. Preferred capsule or compressed tablet forms generally comprise a therapeutically effective amount of the crystalline forms of Compound (I) and one or more disintegrants in an amount greater than about 10% by weight relative to the total weight of the contents of the capsule or the total weight of the tablet.

Preferred capsule formulations may contain the crystalline forms of Compound (I) in an amount from about 5 to about 1000 mg per capsule. Preferred compressed tablet formulations contain the crystalline forms of Compound (I) in an amount from about 5 mg to about 800 mg per tablet. More preferred formulations contain about 50 to about 200 mg per capsule or compressed tablet. Preferably, the capsule or compressed tablet pharmaceutical dosage form comprises a therapeutically effective amount of Form N-3 of Compound (I); a surfactant; a disintegrant; a binder; a lubricant; and optionally additional pharmaceutically acceptable excipients such as diluents, glidants and the like; wherein the disintegrant is selected from modified starches; croscarmallose sodium, carboxymethylcellulose calcium and crospovidone.

For oral administration in liquid form, the crystalline forms of Compound (I) can be combined with any oral, non-toxic pharmaceutically acceptable inert carrier such as ethanol, glycerol, water and the like. The liquid composition may contain a sweetening agent which to make the compositions more palatable. The sweetening agent can be selected from a sugar such as sucrose, mannitol, sorbitol, xylitol, lactose, etc. or a sugar substitute such as cyclamate, saccaharin, aspartame, etc. If sugar substitutes are selected as the sweetening agent the amount employed in the compositions of the invention will be substantially less than if sugars are employed. Taking this into account, the amount of sweetening agent may range from about 0.1 to about 50% by weight, and all combinations and subcombinations of ranges and specific amounts therein. Preferred amounts range from about 0.5 to about 30% by weight.

The more preferred sweetening agents are the sugars and particularly sucrose. The particle size of the powdered sucrose used has been found to have a significant influence in the physical appearance of the finished composition and its ultimate acceptance for taste. The preferred particle size of the sucrose component when used is in the range of from 200 to less than 325 mesh US Standard Screen, and all combinations and subcombinations of ranges and specific particle sizes therein.

Sterile injectable solutions may be prepared by incorporating the crystalline forms of Compound (I) in the required amounts, in the appropriate solvent, with various of the other ingredients enumerated herein, as required, followed by filtered sterilization. Generally, dispersions may be prepared by incorporating the sterilized active ingredient into a sterile vehicle which contains the dispersion medium and any other required ingredients. In the case of sterile powders for the preparation of sterile injectable solutions, the preferred methods of preparation may include vacuum drying and the freeze drying technique which may yield a powder of the active ingredient, plus any additional desired ingredient from the previously sterile-filtered solution thereof.

As would be apparent to a person of ordinary skill in the art, once armed with the teachings of the present disclosure, when dissolved, Compound (I) loses its crystalline structure, and is therefore considered to be a solution of Compound (I). All forms of the present invention, however, may be used for the preparation of liquid formulations in which Compound (I) may be, for example, dissolved or suspended. In addition, the crystalline forms of Compound (I) may be incorporated into solid formulations.

The liquid compositions may also contain other components routinely utilized in formulating pharmaceutical compositions. One example of such components is lecithin. Its use in compositions of the invention as an emulsifying agent in the range of from 0.05 to 1% by weight, and all combinations and subcombinations of ranges and specific amounts therein. More preferably, emulsifying agents may be employed in an amount of from about 0.1 to about 0.5% by weight. Other examples of components that may be used are antimicrobial preservatives, such as benzoic acid or parabens; suspending agents, such as colloidal silicon dioxide; antioxidants; topical oral anesthetics; flavoring agents; and colorants.

The selection of such optional components and their level of use in the compositions of the invention is within the level of skill in the art and will be even better appreciated from the working examples provided hereinafter.

The crystalline forms of Compound (I) may also be coupled with soluble polymers as targetable drug carriers. Such polymers can include polyvinylpyrrolidine pyran copolymer, polyhydroxypropylmethacrylamide-phenol, polyhydroxyethyl-aspartamidephenol or polyethylene oxide-polylysine substituted with palmitolyl residues. Gelatin capsules of the crystalline forms of Compound (I) may contain the crystalline Compound (I) and the liquid or solid compositions described herein. Gelatin capsules may also contain powdered carriers such as lactose, starch, cellulose derivatives, magnesium stearate, stearic acid and the like. Similar diluents can be used to make compressed tablets. Both tablets and capsules can be manufactured as sustained release products to provide for continuous release of medication over a period of hours. Tablets can be sugar coated or film coated to mask any unpleasant taste and to protect the tablet from the atmosphere or enteric coated for selective disintegration in the gastrointestinal track.

In general, water, a suitable oil, saline, aqueous dextrose (glucose), and related sugar solutions and glycols, such as propylene glycol or polyethylene glycols are suitable carriers for parenteral solutions. Solutions for parenteral solutions are prepared by dissolving the crystalline Efavirenz in the carrier and, if necessary, adding buffering substances. Anti-oxidizing agents such as sodium bisulfite, sodium sulfite, or ascorbic acid either alone or combined, are suitable stabilizing agents. Citric acid and its salts and sodium EDTA may also be employed. Parenteral solutions may also contain preservatives, such as benzalkonium chloride, methyl- or propyl-paraben and chlorobutanol.

Suitable pharmaceutical carriers are described in Remington's Pharmaceutical Sciences, Mack Publishing Co., the disclosures of which are hereby incorporated herein by reference, in their entireties.

The preferred crystalline form of Compound (I) may serve as component (a) of this invention and can independently be in any dosage form, such as those described above, and can also be administered in various combinations, as described above. In the following description component (b) is to be understood to represent one or more agents as described herein suitable for combination therapy.

Pharmaceutical kits which may be useful for the treatment of various disorders, and which comprise a therapeutically effective amount of a pharmaceutical composition comprising a novel form of Compound (I) in one or more sterile containers, are also within the ambit of the present invention. The kits may further comprise conventional pharmaceutical kit components which will be readily apparent to those skilled in the art, once armed with the present disclosure. Sterilization of the container may be carried out using conventional sterilization methodology well known to those skilled in the art.

The present invention is further described in the following examples. All of the examples are actual examples. These examples are not to be construed as limiting the scope of the appended claims.

EXAMPLES

Example 1

Method 1 for Preparation of Form P-1

25 g of Compound (I) was charged to a 1 L Morton flask equipped with a mechanical stirrer. 261.25 mL of acetic acid and 13.75 mL of de-ionized water were added to the flask. The mixture was agitated at 150 rpm and heated to 80° C. After approximately 1 hour, the solid was dissolved. The mixture was cooled to 70° C. and 0.5 g of seed was added. The agitation rate was reduced to 100 rpm. 300 mL of EtOH was added to the sample over an 1 hour period. The mixture was cooled to 20° C. over 2 hours and held at 20° C. for 4 hours. The slurry was filtered. The wet cake was washed with 125 mL of EtOH, and dried at 70° C. under vacuum overnight. Weight of dried cake was 22.87 g. Yield was 89.5 M %.

Example 2

Method 2 for Preparation of Form P-1

Form P-1 of Compound (I) was prepared by crystallization of Compound (I) from acetone, methanol, dichloromethane, or acetic acid. For example, 1 gram of Compound (I) was dissolved in 20 mL of acetic acid at 80° C. The acetic acid solution was cooled from 80° C. to 20° C. over two hours. The slurry was stirred overnight and filtered. The wet cake was dried in a vacuum oven at 70° C. overnight. XRPD patterns showed the dried crystalline powder was Form P-1.

Example 3

Preparation of Form P-2

The following solvents were added in order to dissolve 20 mg of Compound (I): 1 ml THF, 1 ml toluene, 0.5 ml 1-methyl-2-pyrrolidinone, 0.5 ml acetone. Compound (I) had little solubility in these solvents even with heating. A clear solution was achieved after adding MeOH and heating. The solution was kept sealed at 60.5° C. and then at room temperature 3 days later. Fiber-like crystals were observed within ~7 days. This is P-2 form.

The P-2 form was also reproduced by crystallizing:
1. 15 mg of Compound (I) in 0.5 ml DMF, and small amounts of water, NMP, acetonitrile with heating of the solution;
2. 40 mg of Compound (I) in 1 ml MeOH, 0.5 ml water, 1 ml acetonitrile, and 1.5 ml NMP;
3. 30 mg of Compound (I) in 1 ml DMF and 1 ml NMP;
4. 40 mg of Compound (I) in 1 ml NMP, 0.5 ml water, and 1 ml acetonitrile;
5. 40 mg of Compound (I) in 1 ml acetonitrile and 1 ml NMP; or
6. 35 mg of Compound (I) in 2 ml acetonitrile, 0.5 ml water, and 1.5 ml NMP.

Example 4

Method 1 of Preparation of Form P-3

The Form P-3 of Compound (I) was prepared by suspending 100 mg of Form P-1 in 5 mL tetrahydrofuran in a glass vial for 7 days. The suspension was filtered and yielded the P-3 form was obtained.

Example 5

Method 2 of Preparation of Form P-3

100 mg of Compound (I) was dissolved in 110 mL of THF at 65° C. The THF solution was cooled from 65° C. to 20° C. over 90 min and stirred overnight. The slurry was filtered. The wet cake was dried at 30° C. under vacuum. XRPD assay of the dried powder showed that it was a P-3 form.

Example 6

Preparation of Form P-4

P-4 form can be obtained by recrystallization from DMF/water. 0.1 g of Compound (I) was dissolved in 4 mL of DMF at 75° C. and 1 mL of water was added. The solution was stirred at 75° C. for 12 minutes. Another 1 mL of water was then added. The solution was stirred for 18 minutes and then cooled to 20° C. over 1 hour. The slurry was filtered and dried in vacuum oven. NMR data showed that it contains 0.44 mole of DMF per mole of 1-(4-benzoyl-piperazin-1-yl)-2-[4-methoxy-7-(3-methyl-[1,2,4]triazol-1-yl)-1H-pyrrolo[2,3-c]pyridin-3-yl]-ethane-1,2-dione.

What is claimed is:

1. Form P-1 of 1-(4-benzoyl-piperazin-1-yl)-2-[4-methoxy-7-(3-methyl-[1,2,4]triazol-1-yl)-1H-pyrrolo[2,3-c]pyridin-3-yl]-ethane-1,2-dione characterized by an X-ray powder diffraction pattern in accordance with that shown in FIG. 1.

2. Form P-1 of 1-(4-benzoyl-piperazin-1-yl)-2-[4-methoxy-7-(3-methyl-[1,2,4]triazol-1-yl)-1H-pyrrolo[2,3-c]pyridin-3-yl]-ethane-1,2-dione characterized by an X-ray powder diffraction pattern comprising two or more 2θ values selected from the group consisting of: 8.90±0.10, 11.21±0.10, 16.91±0.10 and 21.00±0.10.

3. Form P-1 according to claim 1 or 2 wherein the 1-(4-benzoyl-piperazin-1-yl)-2-[4-methoxy-7-(3-methyl-[1,2,4]triazol-1-yl)-1H-pyrrolo[2,3-c]pyridin-3-yl]-ethane-1,2-dione is substantially pure.

4. Form P-1 according to claim 3, wherein substantially pure is greater than 90 percent pure.

5. Form P-1 of 1-(4-benzoyl-piperazin-1-yl)-2-[4-methoxy-7-(3-methyl-[1,2,4]triazol-1-yl)-1H-pyrrolo[2,3-c]pyridin-3-yl]-ethane-1,2-dione characterized by a differential scanning calorimetry (DSC) thermogram in accordance with that shown in FIG. 2.

6. Form P-1 of 1-(4-benzoyl-piperazin-1-yl)-2-[4-methoxy-7-(3-methyl-[1,2,4]triazol-1-yl)-1H-pyrrolo[2,3-c]pyridin-3-yl]-ethane-1,2-dione characterized by a thermo gravimetric analysis (TGA) diagram in accordance with that shown in FIG. 3.

* * * * *

UNITED STATES PATENT AND TRADEMARK OFFICE
CERTIFICATE OF CORRECTION

PATENT NO. : 7,829,711 B2  
APPLICATION NO. : 12/468105  
DATED : November 9, 2010  
INVENTOR(S) : John D. Matiskella et al.

Page 1 of 1

It is certified that error appears in the above-identified patent and that said Letters Patent is hereby corrected as shown below:

On the Title Page Item (54), line 5, and In the Specification, Column 1, line 5,
change "PYRIDINE" to -- PYRIDIN --.

In the Specification:

Column 1, line 11, change "pending," to -- abandoned, --.

In the Claims:

Claim 2:

Column 16, line 6, change "20" to -- 2θ --.

Signed and Sealed this
Fourth Day of March, 2014

Michelle K. Lee
*Deputy Director of the United States Patent and Trademark Office*